(12) United States Patent  
Meredith et al.

(10) Patent No.: US 8,189,876 B2  
(45) Date of Patent: May 29, 2012

(54) SEDIMENT ASSESSMENT

(75) Inventors: William Neville Eugen Meredith, Thirsk (GB); John Carroll, Stockton-on-Trees (GB); Stephen Derek Rogers, Seaham (GB)

(73) Assignee: Brunob II BV, Arnhem (NL)

( * ) Notice: Subject to any disclaimer, the term of this patent is extended or adjusted under 35 U.S.C. 154(b) by 1007 days.

(21) Appl. No.: 11/660,990

(22) PCT Filed: Aug. 18, 2005

(86) PCT No.: PCT/GB2005/003250  
§ 371 (c)(1), (2), (4) Date: Dec. 18, 2007

(87) PCT Pub. No.: WO2006/021758  
PCT Pub. Date: Mar. 2, 2006

(65) Prior Publication Data  
US 2008/0137904 A1 Jun. 12, 2008

(30) Foreign Application Priority Data  
Aug. 26, 2004 (GB) .................................. 0419059.1

(51) Int. Cl.  
G06K 9/00 (2006.01)  
G06K 9/36 (2006.01)  
C08B 30/00 (2006.01)  
G01B 11/30 (2006.01)

(52) U.S. Cl. ........ 382/110; 382/100; 382/141; 382/286; 127/65; 127/69; 127/71; 356/600

(58) Field of Classification Search .......................... None  
See application file for complete search history.

(56) References Cited

U.S. PATENT DOCUMENTS

| | | | | |
|---|---|---|---|---|
| 3,661,640 | A | * | 5/1972 | Griffith et al. .................. 127/28 |
| 3,836,376 | A | * | 9/1974 | Hampton et al. .......... 106/214.2 |
| 4,188,466 | A | * | 2/1980 | Thivend et al. .................. 435/18 |
| 4,281,109 | A | * | 7/1981 | Jarowenko et al. ............. 536/50 |
| 4,710,874 | A |   | 12/1987 | Cinqualbre |
| 4,713,781 | A | * | 12/1987 | Brizgis et al. ................. 382/110 |
| 4,827,099 | A | * | 5/1989 | Krebs et al. .............. 219/121.63 |
| 4,943,160 | A | * | 7/1990 | Gevelber et al. .............. 356/625 |
| 5,198,035 | A | * | 3/1993 | Lee et al. ......................... 127/67 |
| 5,314,825 | A | * | 5/1994 | Weyrauch et al. .............. 436/43 |

(Continued)

FOREIGN PATENT DOCUMENTS  
DE 10218693 A1 8/2003

(Continued)

OTHER PUBLICATIONS  
Corresponding Japanese Office Action mailed Aug. 31, 2010.

(Continued)

*Primary Examiner* — Michelle Entezari  
(74) *Attorney, Agent, or Firm* — Jones Day

(57) ABSTRACT

There are described methods and apparatus for assessing sediments generated in liquid-based systems. The methods involve optically obtaining information to enable height and, thus, volume data relating to sediments to be measured. Although single samples of liquid-based systems may be processed the methods are particularly suited to processing multiple samples to obtain data relating to sediments at a high rate. The apparatus includes automated handling equipment to enable samples to be moved between workstations and relative to associated optical equipment that is used to obtain information relating to the sediments.

16 Claims, 2 Drawing Sheets

U.S. PATENT DOCUMENTS

Figure 1:
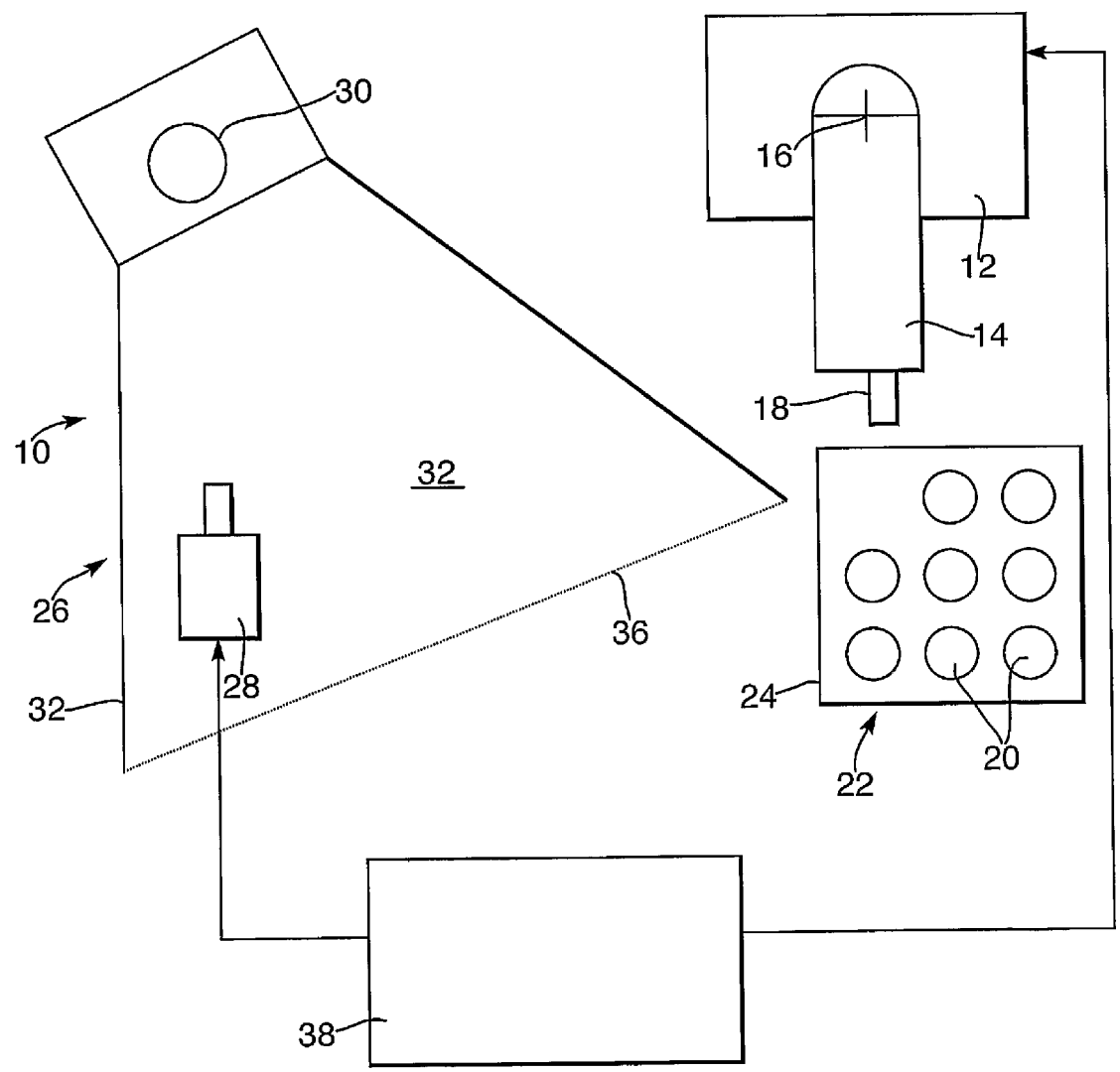

| | | | | |
|---|---|---|---|---|
| 5,768,407 A * | 6/1998 | Shen et al. | | 382/133 |
| 6,197,523 B1 * | 3/2001 | Rimm et al. | | 435/7.1 |
| 6,646,264 B1 * | 11/2003 | Modiano et al. | | 250/339.07 |
| 6,683,694 B2 * | 1/2004 | Cornil | | 356/627 |
| 6,929,953 B1 * | 8/2005 | Wardlaw | | 436/63 |
| 6,965,689 B2 * | 11/2005 | Lee et al. | | 382/154 |
| 7,205,529 B2 * | 4/2007 | Andersen et al. | | 250/223 R |
| 7,212,654 B2 * | 5/2007 | Hodgson et al. | | 382/110 |
| 7,223,356 B2 * | 5/2007 | Chartier et al. | | 252/500 |
| 7,508,423 B2 * | 3/2009 | Ohmori et al. | | 348/230.1 |
| 2002/0012117 A1 * | 1/2002 | Wardlaw | | 356/39 |
| 2003/0191298 A1 * | 10/2003 | Barash et al. | | 536/23.1 |
| 2004/0109612 A1 * | 6/2004 | Park et al. | | 382/254 |
| 2004/0194302 A1 * | 10/2004 | Bhullar et al. | | 29/847 |
| 2004/0252870 A1 * | 12/2004 | Reeves et al. | | 382/128 |
| 2005/0002552 A1 * | 1/2005 | Dunn et al. | | 382/133 |
| 2005/0025356 A1 * | 2/2005 | Fukuda | | 382/167 |
| 2005/0070005 A1 * | 3/2005 | Keller | | 435/252.1 |
| 2006/0193515 A1 * | 8/2006 | Kim et al. | | 382/173 |
| 2006/0239533 A1 * | 10/2006 | Tafas et al. | | 382/133 |

FOREIGN PATENT DOCUMENTS

| | | |
|---|---|---|
| EP | 0755654 A1 | 1/1997 |
| EP | 0864854 | 9/1998 |
| JP | 08178729 | 7/1996 |
| JP | 09133687 A | 9/1997 |
| JP | 11248853 | 9/1999 |
| JP | 2001165752 A | 6/2001 |
| WO | WO 03/031938 | 4/2003 |

OTHER PUBLICATIONS

International Search Report dated Jan. 26, 2006 for PCT/GB2005/003250.

Office Action from the Chinese Patent Office dated Sep. 21, 2010.

Search Report for GB0419059.1 dated Nov. 8, 2004.

* cited by examiner

SEDIMENT ASSESSMENT

CROSS REFERENCE TO RELATED APPLICATION

This application is the National Phase application of International Application No. PCT/GB2005/003250, filed Aug. 18, 2005, which designates the United States and was published in English. This application, in its entirety, is incorporated herein by reference.

The invention relates to the measurement and assessment of sediment volumes.

There is significant interest in deriving information from sediment volumes. For example, sediment volume is an important parameter for many multi-component liquid-based systems. It is a key measurement for the water industry where it is used to assess the need for extra filtration or additive addition and as a quality control in the supply of drinking water. Measurement of a sediment volume is also used to assess the quality of products such as beer and wine.

In other applications, the swelling volume of a component in a multi-component liquid-based system is an important measure of the degree to which materials swell on hydration. It is used extensively in the food industry for characterising the behaviour of different flours and natural or synthetic starches and mixtures thereof, as an indication of performance in baking, thickening properties etc. Swelling volume is typically measured as a volume to a dry weight of the component added to the system, ie ml/gm.

In other multi-component liquid-based systems, it may be necessary to aid sedimentation prior to determining the sediment volume. This may be achieved using flocculants. In some systems flocculation will occur naturally with certain particulate suspensions. Other systems require the addition of flocculants to clear small particles that will either not sediment or only sediment slowly from liquid products. Once flocculation has occurred, sedimentation will take place and the quantity of particles present can be assessed by measuring the sediment volume.

In other applications, it may be important to determine the volume of precipitated or crystallised components from liquid-based systems.

Typical examples of components that may form sediments are flours, natural or synthetic starches, metal oxides, eg $TiO_2$, $SiO_2$, $Al_3O_2$, ceramic powders, clays, eg kaolinite clays (china clay, ball clay), montmorillonites, talc etc.

It will be appreciated from the above description that the present invention is applicable to a wide range of sediments and, for the avoidance of doubt, the term "sediment" as used in this specification is intended to cover sediments, with or without flocculants, and precipitated and crystallised materials The rate-determining step in determining many sediment volumes is the generation and settlement of the sediment itself. For example, in measuring starch sediments, a standard period of 24 hours is used to permit sedimentation to occur. This technique is described in a paper by A Tayal, R Shariff and J Whaley, "Modelling properties of Viscosifying Starches", Gums and Stablisers for the Food Industry 12, 23-27 Jun. 2003, 97-107. Furthermore, standard techniques for determining sediment volume use relatively large quantities of materials and, consequently, do not lend themselves to the generation of relatively large numbers of samples and the subsequent rapid assessment of such samples.

It is an object of the present invention to provide a method of assessing sediment volumes in liquid-based samples that is consistent across samples and is reasonably fast.

The Applicants have found that the sediment volume in liquid-based samples can be repeatedly achieved and matches results obtained from standard methods using image analysis techniques. Although image analysis techniques, for example for agglutination reactions and phase-separated systems, are known, eg U.S. Pat. No. 4,794,450, U.S. Pat. No. 5,768,407, U.S. Pat. No. 5,783,826, EP-A-0755654, DE-A-10218693, JP-A-2001165752, JP-A-09133687, WO 01/04608 and WO 2004/053468, such techniques have not been used to determine sediment volume.

According to the present invention, a method of assessing sediment volume in a liquid-based sample comprises:

a) positioning a tube containing the sample relative to an opto-electrical device capable of capturing an image of the tube;
b) using the opto-electrical device to capture an image of the tube normal thereto;
c) analysing the captured image to determine the height of the sediment; and
d) using the height measurement to generate a sediment volume measurement.

The term "tube" as used herein means any conveniently shaped receptacle capable of holding a relatively small sample of liquid-based systems (including any sediment generated therein) and having a constant cross-sectional area over its length. As it needs to be optically transparent, it is suitably made from glass or other optically transparent material that is effectively chemically inert to the liquids under test. Conveniently, the tube is a glass vial typically having a length of 55 mm, and has an external diameter of 17 mm, internal radius of 7.6 mm and a generally flat bottom.

Preferably, the analysis of the captured image comprises converting the captured image (image 1) in to a binary image (image 2) and measuring the area and the width of the portion of a binary image corresponding to the sediment. Simply dividing the area by the width derives the height of the sediment. The height measurement is then used in combination with the cross-sectional area of the tube to determine the sediment volume.

The image captured by the opto-electronic device is preferably subjected to analysis by suitable software, for example the KS300 Image Analysis System available from Carl Zeiss Vision GmbH, Hallbergmoos, Germany. The software is configured to analyse the image for the information of interest.

Image 1 may be obtained as a black and white image or as a colour image that is processed to be a black and white image. The colour image may be processed by selecting at least one information channel (red, green or blue) of the digital image and creating therefrom the black and white image 1 in an electronic frame.

Preferably, however, image 1 is initially generated as a grey scale black and white image that is then automatically converted to a binary image 2. To aid the conversion process by ensuring the central region of the anticipated sediment element of image 1 is neither too bright (ie white) nor too dark, the opto-electrical device is set to limit the pixel intensity of the image 1 in that region. The pixel intensity may suitably be set to about 60% to 90% of the pixel intensity range of the opto-electronic device (which equates to a pixel intensity range of about 170 to 230 (black is 0 and white is 255) when using an eight bit camera for example). In one embodiment, the range may be initially set to 75% to 82% and conveniently to 78% of the range. In another, more preferred embodiment, the range is initially set to about 65% to 75% of said range. Conveniently, in this embodiment, the pixel intensity level may be set around 70% of the range.

The method may include subsidiary steps to improve the quality of the images being processed. For example, if the lighting used during capture of the image of the tube results in a shading across the image, image 1 is subjected to a partial smoothing operation, eg using a median filter, to remove some detail but to retain edge information thereby generating a smoothed image (image 1a). It is the image 1a that is subjected to the automatic conversion to binary image 2.

Binary image 2 may then be subjected to a scrap operation to remove small white features within the black areas and a fill operation to fill in holes in the white objects so they are more complete (image 3).

Image 3 may then be edited to remove any features associated with any glare due to the glass wall at the bottom of the tube and to reconstruct of the bottom region of the sediment in the vial. The latter step may be required if the sediment in the bottom of the tube does not scatter well and, consequently, may be missing from the binary image 2. As there is always sediment in the bottom of the tube and as the position of the tube in image 2 is always the same, then a constant edit can be applied to the image 3 to generate a corrected binary image 4.

As the vertical edges of the sediment may be slightly non-linear and as this may affect the measurement of the width of the sediment, and hence the height determination, a new binary image (image 5) is created consisting of a white or black rectangle whose axis is along the axis of the tube and whose width is less than the width of the sediment. A Boolean AND operation is then performed using images 4, following an inversion operation if applicable, and 5 to create image 6 which is an image of the central section of the sediment.

The height of the sediment is determined from image 6 by measuring the area and the width of the white central section. As the top surface of the sediment is not always flat, there is an issue of where to measure the height if only a single point is employed. Using the above-described technique, the height is therefore measured over the whole width of the white central section in the final binary image.

Once the height of the sediment in the sample is known, the sediment volume is derived from the height measurement and the cross-sectional area of the tube.

Thus, the present invention also includes a method of determining the height and/or the volume of sediment formed in a liquid-based sample in a tube which comprises subjecting a digital, binary image of the sediment in the tube to the following electronic operations:

a) copying the digital binary image (image 1) into an electronic frame (image 2) and then clearing image 2 from this frame to create a new blank frame having the same pixel dimensions as the original digital image 1;
b) creating a rectangle in a graphics plane associated with the electronic frame and merging the graphics plane with the image plane of image 2 and specifying the rectangle is white or black and the remainder is black or white, respectively, thereby creating a binary image (image 3) of a rectangle on a contrasting background, the rectangle having dimensions longer than the anticipated length of the sediment being measured and narrower than the width of the internal dimension of the tube;
c) subjecting image 1, after an inversion operation if required, and image 3 to a Boolean "AND" operation to create an image (image 4) representative of the sediment height; and
d) measuring the dimensions of the rectangle in image 4 to determine the sediment height and, if required, the sediment volume.

It will be appreciated that images 1, 3 and 4 identified in the preceding paragraph are equivalent to images 4, 5 and 6 as previously described with respect to the method of assessing sediment volume in accordance with the invention.

Preferably, in step b), the rectangle is white and the remainder is black.

Depending upon the sedimentary systems being studied, the quality of the binary images initially obtained from the original grey scale image may vary significantly. For example, sedimentary systems of starches may give rise to a variety of image types and these binarise differently to give the binary image. Sometimes it is found that the binary representation of the grey scale sediment region is seen by the eye to be poor and in order to obtain a good representation the conditions employed during initial image capture need to be altered. For instance, the image may be good, ie it will have a well settled sediment and a clear supernatant; or the supernatant may be hazy owing to starch fines not settling giving rise to a diffuse sediment/supernatant interface; or the sediment may contain white specks that exhibit a high pixel intensity.

Accordingly, in a preferred embodiment of the invention, prior to determining the height of the sediment, the quality of the captured image is checked. If the image is of poor quality, it may be rejected or, alternatively, the image may be captured and book marked for subsequent manual examination.

Preferably, an initial check of the image quality is made to determine whether the maximum pixel intensity ($I_{max}$) within a predefined region of sediment is within a required range (typically within the range 70% to 75% of the total pixel intensity range). If $I_{max}$ is within the required range, then the quality of the image is checked further as described below. However, if $I_{max}$ is above the required range, then the lighting level is reduced and/or the camera settings (e.g. exposure time) employed during image capture is decreased in an iterative process until an acceptable image is acquired. Similarly, if $I_{max}$ is below the required range, then the lighting level is increased and/or the exposure time employed during image capture is increased in an iterative process until an acceptable image is acquired.

It will be appreciated that, in the event of the limits of adjustability being reached, the final image is captured, stored and bookmarked for subsequent examination.

Once an image with an $I_{max}$ within the required range is obtained, then preferably, the quality of the image is checked further by superimposing a series of vertical lines over the binary representation of the sediment, measuring the lengths of the lines and obtaining a standard deviation for those lengths. If the standard deviation is greater than a selected standard deviation, the image is of poor quality and the sediment volume determination from such an image is suspect. The selected standard deviation used for comparison purposes is obtained by checking a series of good and bad images and selecting a standard deviation above which the image quality is unacceptable.

As discussed above, the issue of poor quality images usually arise if the operation to generate a binary image from the captured image results in a poor binary image. This latter image gives rises to high standard deviations. The quality of the captured image may be improved by varying the illumination of the tube. However, if variation of the illumination of the tube still does not result in an acceptable image, then the sample may be rejected or captured and book marked as mentioned above.

In a preferred embodiment, if the binary image is poor, ie has a standard deviation greater than the selected standard deviation, the mean pixel intensity ($I_{mean}$) is measured for a designated area within the image and either:

a) if the $I_{mean}$ is within the required $I_{max}$ range, reduce the light intensity and capture a new image of the sediment for processing; or b) if the $I_{mean}$ is outside a second $I_{max}$ range (defined as the preselected $I_{max}$, say 70% of the pixel intensity range as described above, ± a selected % age, say 5%), increase the light intensity and capture a new image of the sediment for processing.

Steps a) and b) in the preceding paragraph are iterative in that, if an acceptable image is not obtained after a first light intensity adjustment, the relevant step is repeated. With regard to step a), in the event of an acceptable image not being achieved when $I_{mean}$ falls below a predefined minimum value, for example 40% of the pixel intensity range, the process is terminated but the final image is captured and book marked as described above. With regard to step b), it is iterated until $I_{mean}$ falls within the second $I_{max}$ range or, if the light intensity is at the maximum available, the process is terminated but the final image is captured and bookmarked as described above.

In step a), it is assumed that the high standard deviation is caused by flare from particles in the supernatant, ie a hazy supernatant as described above in relation to starch sedimentary systems, whereby the reduction in light level will reduce the amount of light reflect from such particles in the supernatant.

In step b), it is assumed the sediment has specific areas that give rise to locally high values of $I_{max}$, ie white specks as described above in relation to starch sedimentary systems, whereby the increase in the light intensity will result in the remainder of the sediment giving rise to an increased background $I_{mean}$.

The designated area of the image within which $I_{mean}$ is measured it usually determined by examination of a number of typical samples and determining the boundaries of the meniscus positions and the tube bottom.

Using the method of the invention, a typical sediment volume measurement time is under a minute, typically about 40 seconds from the initial placing of the sample to its final removal from the sample holder. Where the sediments are well settled and the supernatants non-hazy, the process can take less time, in the region of 10 to 20 seconds. Owing to the simplicity of the method, a large number of samples can be tested in a short time period. The samples may be tested singly and sequentially or, alternatively, and more preferably, batches of samples can be tested in parallel. Accordingly, the method of the invention includes processing batches of samples either sequentially or in parallel. When the samples are processed in parallel, preferably more than 1 sample but not more than 100 samples, more preferably at least 10 samples but not more than 50 samples are processed together.

Whilst it would be possible to provide sufficient opto-electronic devices to measure the sediment volumes of a number of samples, it is preferred to minimise the number of such devices used in the method. Accordingly, it is preferred, in each batch of samples, each tube is sequenced in turn to capture the image of the sediment in that tube.

Although the invention has utility in relation to a wide variety of sedimentary systems, the Applicant has found it of especial utility in relation to starch-based sedimentary systems. Accordingly, in a particularly preferred embodiment, the sample comprises a natural or synthetic starch or mixture of starches dispersed in water as described earlier.

According to another aspect of the present invention, apparatus for determining sediment volume formed in a liquid-based sample comprises a tube open at one end for receiving liquid samples that generated sediments, an opto-electronic device located in use adjacent the tube, said opto-electronic device being capable of capturing an image of the tube, and control means capable of receiving said image and being operable to analyse the image so received to provide a measurement of sediment volume.

The opto-electronic device capable of capturing images is conveniently an electronic camera, for instance a charge coupled device (CCD) camera or a complementary metal oxide semiconductor (CMOS) chip-containing camera, either having an analogue or digital output. As it needs to generate an image of the tube from which sediment height is determined, the device is conveniently a low-resolution black and white camera, for example a camera having a pixel resolution of 752×582. For example, a Sony XC-75CE using a Pentax 25 mm f1.4 lens is a suitable camera. However, if desired, medium- or high-resolution cameras, for example a camera having a pixel resolution of 1300×1030, may be used. For example, an AxioCam MRC available from Carl Zeiss Vision GmbH would be a suitable camera.

As will be well understood, suitable lighting has to be provided to enable the images to be captured. Conveniently, two light sources are used. The first source is front lighting (relative to the camera position) but at an offset position to avoid back reflection of the light to the camera is provided during image capture. A suitable light source is a cold cathode LP-100 lamp available from Universal Electronics Industries Ltd. The second source is positioned directly below the tube and a suitable light source is a Schott cold light source with a gooseneck fibre optic cable.

It is preferred that extraneous light sources are excluded to avoid back reflections that may affect the quality of the captured image. Preferably, a surrounding non-reflective environment is provided to minimise further the possibility of extraneous reflections being captured as part of the images.

In preferred embodiments of the apparatus according to the invention, the apparatus further comprises a workstation at which is located the opto-electronic device or devices and automated handling equipment for moving the tube relative to said workstation and for positioning the tube relative to the opto-electronic device, said control means being adapted to control said automated handling equipment to move the tube to and from the workstation and to move the tube and the opto-electronic device or devices relative to one another.

Preferably, the control means is operable to automatically check the quality of images captured by the opto-electronic device as described above in relation to the method according to the invention and to vary the illumination of the tube and/or reject the tube and/or book mark the sediment volume determination of that sample.

The present invention, in yet another aspect, encompasses apparatus for assessing sediment volume in a liquid-based system comprises a workstation at which is located an opto-electronic device capable of generating an image of a tube containing a sample of a sedimented liquid-based system, automated handling equipment for moving a tube relative to said workstation and control means for initiating action in response to input from the opto-electronic device and being adapted to control said automated handling equipment to move a tube to and from the workstation and relative to the opto-electronic device whilst it is located at the workstation, said control means being capable of receiving said image and being operable to analyse the image so received to provide a measurement of sediment volume.

Automated sample handling is achieved using, for instance, a Zymark XP tracked robot system, available from Zymark Corporation, Zymark Center, Hopkinton, Mass. 01748 USA, with a variety of associated workstations. Control of the system and the opto electronic device is carried out by means of Easylab robot control programming language. However, a range of other robotic systems could be employed.

Associated with the or each workstation may be liquid supply means such as liquid injectors to enable samples to be introduced to the sample tubes and to provide automated waste disposal. Alternatively, racks of sample tubes may be prepared remotely from the workstation and the racks can then be introduced to a workstation accessible by the automated handling means. Following use, the sample tubes may then be disposed off, this being more economical than cleaning the sample tubes and re-using them.

Figure 2:
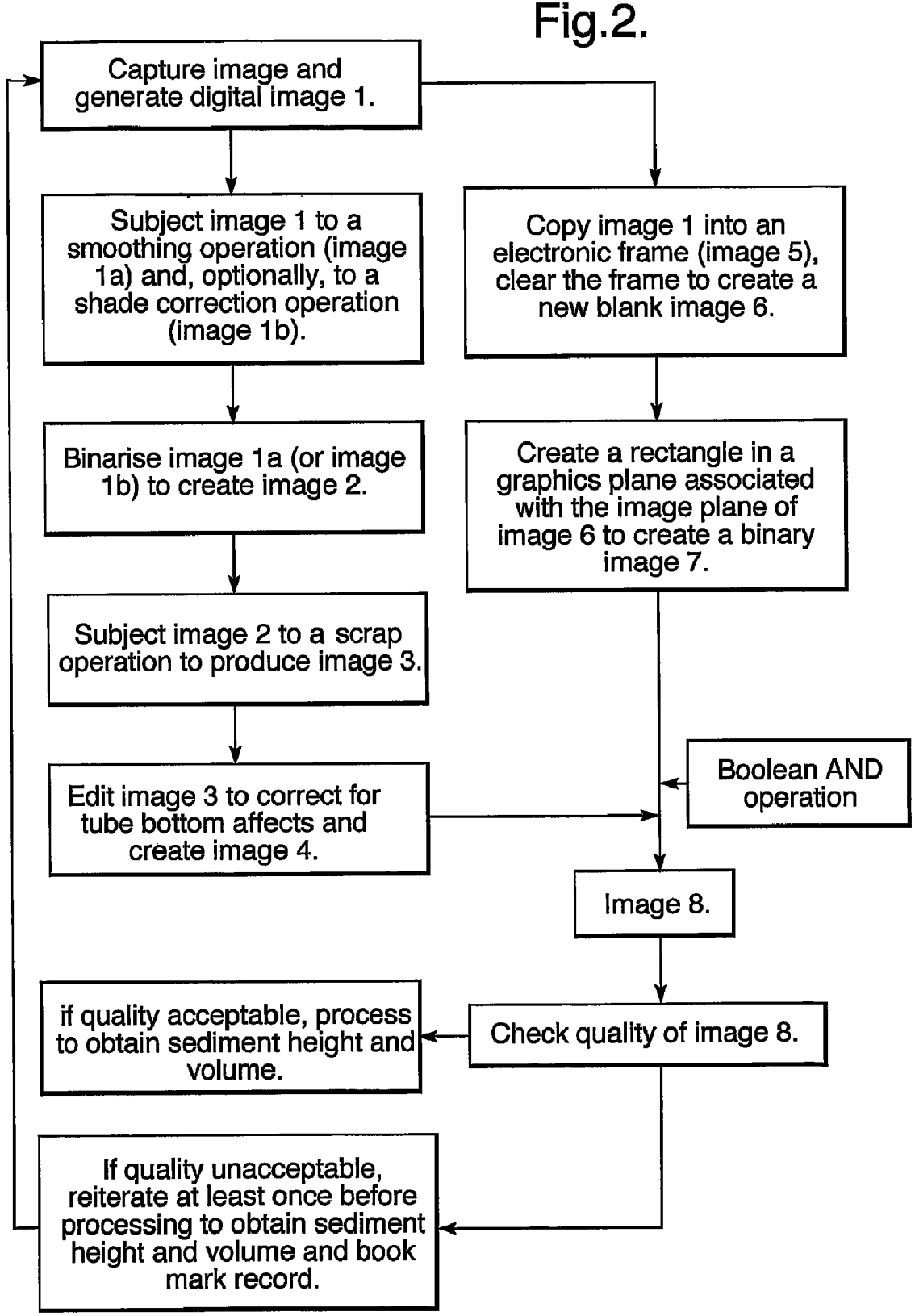

The invention will now be illustrated by reference to the drawing and following examples. The drawings are:

FIG. 1 is a schematic plan view of automated sample handling and measuring apparatus according to the invention; and FIG. 2 is a flow diagram of the general sequences used to capture images of tubes and to process them to obtain information relating to the sediment as described in Example 1.

In FIG. 1, is shown an automatic sample handling and testing apparatus in accordance with the invention. The apparatus 10 has a Zymark XP robot system 12 in which the robot arm 14 is mounted both for rotation about a vertical axis 16 and in the direction of said axis 16. One end of the arm 14 has a gripper mechanism 18 by which sample tubes 20 can be gripped.

Rotation of the robot arm 14 about the axis 16 enables one or more workstations to be accessed. The number of workstations in the apparatus 10 can be varied to suit the application. In FIG. 1, the apparatus 10 is shown as having the following workstations:

a tube holding station 22 at which a rack of 24 of sample tubes 20 are located; and
an image capture and analysis station 26 at which are located a camera 28 and a holder 30 for a sample tube 20.

The camera 28 was an eight bit CCD camera that was capable of capturing images of the tube containing the sediment. Camera 28 was a Sony XC-75CE fitted with a Pentax 25 mm f1.4 lens located about 280 to 350 mm from the tube 20. To prevent unwanted reflections being captured as parts of the images of the tubes (and sediments), station 26 was surrounded by a non-reflective, light neutral environment including sidewalls 32, a top (not shown), bottom 34 and a front curtain 36 for ease of access. Station 26 was also provided with a cold cathode LP-100 lamp light source positioned above and in front of the tube position relative to the camera 28 so that the sediment is lit from the front and at an angle thereto to minimise stray reflections; and a Schott cold light source with a gooseneck fibre optic cable the end of which was located immediately beneath the tube.

A control device in the form of a suitable computer system 38 (which may be a single computer or may be more than one computer) is used to control the robot system 12 and to control the camera 28 to capture tube images and to process and store the images and sediment volumes determined therefrom. The images were processed using Zeiss KS300 image analyser software. However, any imaging/image analysis software package can be used including software based on Visual Basic or equivalent packages.

In general, the operation of the apparatus 10 is as follows.

A plurality of sample tubes 20 is located in a rack 24 at the station 22. The tubes 20 contain samples of liquid-based systems that have generated sediments.

It will be appreciated that, in other embodiments of the invention, additional stations at which samples may be introduced into the tubes 20 may be present.

The robot arm 14 is rotated about the axis 16 between the stations 22 and 26 to transfer a sample tube 20 to the station 26 at which an image of the tube is captured Once the sample has been tested, the robot arm 14 returns the sample tube 20 to its location in the rack 24.

The sequence is then repeated for the remaining tubes 20 located at station 22.

Reference is now made to the Examples.

EXAMPLE 1

A rack 24 in which sample-containing glass test tubes 20 (each 55 mm long×17 mm outside diameter) were located was positioned at station 22. The tubes 20 were each sequentially transferred to station 26 at which an image of the tube 20 was captured. The camera 28 was set such that the pixel intensity of the anticipated central part of the sediment could not exceed 200 (78% of the pixel intensity range).

The captured image was stored in the computer system 38 and processed to provide a sediment volume measurement. As part of the processing, the computer checked the quality of the captured image and, if it was not acceptable, adjust light levels and processed a second and, if necessary, subsequent images. If an acceptable image has not been captured and a specified light level has been reached, that image available at that point is captured and processed and the computer records that fact to enable manual examination of the image(s) to be carried out at a later stage.

Analysis of the images was performed using a combination of image processing followed by image analysis using the Zeiss KS300 image analyser software on the computer system 38.

In particular, the image capturing and subsequent processing/analysis was done as follows:

Image Capture 1. capture image* of whole tube 20 using the camera 28 and save this image in a designated file;

* The output from the camera 46 is analogue. The output from the camera 46 is converted into a digital image in a 'framegrabber' board of the computer running the software. It is this digital image that is processed and analysed.

2. check the quality of the image by measuring the $I_{max}$ of the image and determining whether it is within 70% to 75% of the total pixel intensity range and:
    a. if it is within the required range, capture the image for further processing; or
    b. if it is not within the required range:
        i. if $I_{max}$ is above the required range, reduce the lighting level and/or increase the speed of camera shutter and iterate this step until an acceptable image is acquired;
        ii. if $I_{max}$ is below the required range, increase the lighting level and/or decrease the speed of camera shutter and iterate this step until an acceptable image is acquired;
    and, once an acceptable image is acquired, capture the image for further processing and
3. process the captured image to determine sediment volume.

It will be appreciated that, in the event of the limits of adjustability being reached, the final image is captured, stored and bookmarked for subsequent examination.

Sediment Height Analysis 1. subject copy the digital image (image 1) generated by the framegrabber board from the output from camera 28 to a partial smoothing operation, eg using a median filter, to remove some detail but to retain edge information thereby generating a smoothed image (image 1a). It is the image 1a that is subjected to the automatic conversion to binary image 2.

2. binary image 2 is then be subjected to a scrap operation to remove small white features within the black areas and a fill operation to fill in holes in the white objects so they are more complete (image 3);
3. image 3 is then be edited to remove any features associated with any glare due to the wall at the bottom of the tube and to reconstruct of the bottom region of the sediment in the vial. The latter step may be required if the sediment in the bottom of the tube does not scatter well and, consequently, may be missing from the binary image 2. As there is always sediment in the bottom of the tube and as the position of the tube in image 2 is always the same, then a constant edit is applied to the image 3 to generate a corrected binary image 4;
4. copy the digital image (image 1) generated by the framegrabber board from the output from camera 28 into an electronic frame (image 5) and then clear the frame to create a blank image (new image 6) having the same pixel dimensions as the original digital image (image 1);
5. create a rectangle in a graphics plane associated with the electronic frame and merge the graphics plane with the image plane of image 6. Specify the rectangle is white and the remainder is black thereby creating a binary image (image 7) of a white rectangle, the rectangle having dimensions longer than the anticipated length of the sediment being measured and narrower than the width of the internal dimension of the tube and clear the graphics plane of the frame. It is important that the rectangle passes down the central axis of the sediment seen in image 1 but is not as wide as the sediment;
6. subject image 4 and image 7 to a Boolean "AND" operation to create an image (image 8) representative of the sediment height;
7. check the quality of image 8 by superimposing a series of vertical lines over the part of image 8 representing the sediment and measuring the lengths of the lines that fall within the sediment area and obtaining a standard deviation for those lengths. If the standard deviation is greater than a selected standard deviation, the image is of poor quality and the sediment volume determination from such an image is suspect;
8. assessment image quality check in step 7:
   a. if the standard deviation of the image 8 assessed in step 7 is below a selected standard deviation, proceed to step 9; or
   b. if the standard deviation of the image 8 assessed in step 7 is above the selected standard deviation, then measure the $I_{mean}$ of the image 8 and either:
      i. if the $I_{mean}$ is within the required $I_{max}$ range, reduce the light intensity of the Schott cold light source and capture a new image of the sediment and iterate steps 1 to 7; or
      ii. if the $I_{mean}$ is outside a second $I_{max}$ range, ie 70%±5%, increase the light intensity of the Schott cold light source and capture a new image of the sediment and iterate steps 1 to 7; and
   c. if the new image 8 in step 8b)(i) is acceptable, proceed to step 9; if not keep repeating step 8b)(i) until the $I_{mean}$ is below the 40% level of the pixel intensity range and, if the image is still not of the required quality, capture the image in any event and proceed to step 9 but bookmark the record for subsequent manual examination;
   d. if the new image 8 in step 8b)(ii) is acceptable, proceed to step 9; if not keep repeating step 8b)(ii) until the $I_{mean}$ falls within the range or, if the light intensity is at the maximum available, capture the image in any event but bookmark the record for subsequent manual examination.
9. measure image 8 to determine the sediment height; and
10. determine sediment volume.

During the above routine, the software loads the calibration file for camera 28 at this magnification so that distances are correct. This calibration step is performed separately through the capture of an image of a standard scale placed in the exact position usually occupied by the glass tube 20.

The above-described sequences are generally set out in FIG. 2 as a flow chart.

It will be appreciated the various electronic operations used to process the images captured by the camera as described herein, for example invert, thin, open, erode, dilate etc., are well understood in the art. Information relating to such terms is generally available and, in particular, reference is made to "Computer-assisted microscopy: the measurement and analysis of images", John C. Russ, Plenum Press, New York (1990) and "The Image Processing Handbook" 2nd Edition, John C. Russ, CRC Press, Boca Raton (1995). Information on digital camera types can be found in "How to do everything with your digital camera", $3^{rd}$ edition, Dave Johnson, McGraw-Hill, Osbourne (2003).

The materials examined in this Example 1 are listed in Table 1 below together with the sediment volumes determined. For Samples 1 and 2, measured amounts of materials were dispersed in 5 ml of water in the tubes by sealing the end of the tubes and inverting them several times. With regard to Sample 3, this was a pre-formulated dispersion 5 ml of which was placed in a tube. The tubes were allowed to stand for 24 hours before being processed to determine sediment volumes.

EXAMPLE 2

Example 1 was repeated using four modified waxy maize starches available from National Starch and Chemical Co, Bridgewater, N.J., USA. The samples were prepared by dispersing 1 wt % of the starch in 5 ml of water to create a slurry in the tube. The tubes were immersed in a boiling water bath and the slurries were stirred for 3 minutes using glass rods. The tops of the tubes were then covered and the samples were cooked for a further 20 minutes. The tubes were then allowed to stand for 24 hours before being processed as described in Example 1 to determine sediment volumes. The results are given in Table 2 below. In this instance, the sediment volume equates to the swelling volume of the starches.

TABLE 1

| Sample | Material | Weight of material (g) | Height of sediment (mm) | Sediment volume (ml/g) |
|---|---|---|---|---|
| 1 | Gamma polishing $Al_2O_3$ available from Giffin & George Ltd | 0.1848 | 5.27 | 5.26 |
| 2 | Grade 1 $Al_2O_3$ available from Beckman | 2.67 | 14.0 | 0.97 |
| 3 | PTFE dispersion - Grade RAD available from Asahi Glass | 0.21 | 16.0 | 14.05 |

TABLE 2

| Sample | Height of sediment (mm) | Sediment volume (ml/g) |
|---|---|---|
| 4 | 11.91 | 42.3 |
| 5 | 6.06 | 22.2 |
| 6 | 5.68 | 31.0 |
| 7 | 17.78 | 62.8 |

Comparison of the data with data obtained from conventional methods demonstrated the validity of the data obtained using the invention described herein.

EXAMPLE 3

Example 2 was repeated using four cold water swelling starches available from National Starch and Chemical Co, Bridgewater, N.J., USA (Samples 8 to 11). The preparation of the starches was performed at pH 3.0 which is known to give samples with hazy supernatant liquids. The sediment volumes of the samples in the tubes were determined as described in Example 1 except that the camera 28 was set such that the pixel intensity of the anticipated central part of the sediment could not exceed 170 (67% of the pixel intensity range).

The results are given in Table 3 below:

TABLE 3

| Starch | Starting shutter speed (ms) | Imaging shutter speed (ms) | Gooseneck lamp setting | Standard deviation achieved | Calculated sediment height (mm) |
|---|---|---|---|---|---|
| 8 | 50 | 33.5 | 25 | 0.67 | 9.53 |
| 9 | 33 | 5.5 | 25 | 3.2 | 4.8 |
| 10 | 33 | 10.5 | 25 | 4.97 | 5.9 |
| 11 | 33 | 13 | 6 | >5.0: Final image stated to be "too dark" | Height needed to be measured manually from the bookmarked final image |

It will be appreciated that the values of pixel intensity quoted in the description and examples are those preferred by the Applicant and it is within the scope of the invention to select other values of pixel intensity if required.

The invention claimed is:

1. A method of assessing sediment volume in a liquid-based starch-containing sample comprises:
  a) introducing the starch-containing sample into a tube and, if necessary, treating said starch containing-sample to form sediment;
  b) positioning the tube containing the starch-containing sample relative to an opto-electrical device capable of capturing an image of the tube, wherein said starch-containing sample comprises sediment, supernatant, and a sediment-supernatant interface;
  c) using the opto-electrical device to capture an image of the tube normal thereto;
  d) analysing the captured image to determine the height of the sediment; and
  e) using the height measurement to generate a sediment volume measurement.

2. A method according to claim 1 wherein, in step d, the analysis of the captured image comprises converting the captured to a binary image and measuring the area and the width of the portion of the binary image corresponding to the sediment.

3. A method according to claim 1 wherein the opto-electrical device is set to limit the pixel intensity of the captured image in the central region of the anticipated sediment element of the captured image.

4. A method according to claim 3 wherein the pixel intensity is set to about 60% to 90% of the pixel intensity range of the opto-electronic device.

5. A method according to claim 1 wherein, in step d), the captured image is subjected to a partial smoothing operation.

6. A method according to claim 2 wherein the binary image is subjected to a scrap operation to remove small white features within the black areas and a fill operation to fill in holes in the white objects so they are more complete.

7. A method according to claim 1 wherein, in step d), the analysis includes editing the captured image to remove any features associated with any glare due to the wall at the bottom of the tube and to reconstruct of the bottom region of the sediment in the vial.

8. A method according to claim 1 wherein, in step d), the analysis includes creating a new binary image consisting of a white or black rectangle whose axis is along the axis of the tube and whose width is less than the width of the sediment and performing a Boolean AND operation using this image and the binary image of the sediment to create a new binary image which is an image of the height of the central section of the sediment.

9. A method according to claim 8 wherein the height of the sediment is determined by measuring area and the width of the new image.

10. A method according to claim 1 wherein a plurality of starch-containing samples are assessed either sequentially or in parallel.

11. A method according to claim 1 wherein, in parallel assessment, more than 1 starch-containing sample but not more than 100 starch-containing samples, are processed together.

12. A method according to claim 1 wherein, in step d), the quality of the captured image is checked and if it does not meet a predetermined standard, repeating steps c) and d) using different image capture conditions to obtain, if possible, an acceptable image before proceeding to step e).

13. A method according to claim 12 wherein, if the image does not meet the standard after iteration of steps c) and d), the image at that point is captured and that fact is recorded.

14. A method according to claim 12 wherein the image quality is checked by measuring the $I_{max}$ of the image and determining whether it is within a required range of the total pixel intensity range and:
  a) if it is within the required $I_{max}$ range, further processing the image; or
  b) if it is not within the required $I_{max}$ range:
    (i) if $I_{max}$ is above the required $I_{max}$ range, reduce the lighting level and/or increase the speed of image capture and iterate this step until an acceptable image is acquired;
    (ii) if $I_{max}$ is below the required $I_{max}$ range, increase the lighting level and/or decrease the speed of image capture and iterate this step until an acceptable image is acquired;
and, once an acceptable image is acquired, further processing the image.

15. A method according to claim 14 wherein the quality of the image is further checked by superimposing a series of vertical lines over the image of the sediment, measuring the lengths of the lines and obtaining a standard deviation for those lengths and comparing that standard deviation to a pre-selected standard deviation.

16. A method according to claim 15 wherein
 a) if the standard deviation of the image is below a selected standard deviation, further process the image; or
 b) if the standard deviation of the image is above the selected standard deviation, then measure the $I_{mean}$ of the image and either:
  i) if the $I_{mean}$ is within the required $I_{max}$ range, reduce the light intensity and capture a new image of the sediment and iterate capturing and processing an image of the sediment; or
  ii) if the $I_{mean}$ is outside a second $I_{max}$ range, increase the light intensity and capture a new image of the sediment and iterate capturing and processing an image of the sediment; and
 c) if the new image in step b)(i) is acceptable, further process the image; if not keep repeating step b)(i) until the $I_{mean}$ is below a preselected level of the pixel intensity range and, if the image is still not of the required quality, capture the image in any event and further process the image but bookmark the record for subsequent manual examination; or
 d) if the new image in step b)(ii) is acceptable, further process the image; if not keep repeating step b)(ii) until the $I_{mean}$ falls within the range or, if the light intensity is at the maximum available, capture the image in any event but bookmark the record for subsequent manual examination.

\* \* \* \* \*